United States Patent
Hansen et al.

(10) Patent No.: US 6,524,280 B2
(45) Date of Patent: Feb. 25, 2003

(54) DOSE SETTING LIMITER

(75) Inventors: Steffen Hansen, Hillerod (DK); Peter Christian Klitgaard, Smorum (DK)

(73) Assignee: Noro Nordisk A/S, Bagsvaerd (DK)

( * ) Notice: Subject to any disclaimer, the term of this patent is extended or adjusted under 35 U.S.C. 154(b) by 41 days.

(21) Appl. No.: 09/768,760

(22) Filed: Jan. 24, 2001

(65) Prior Publication Data

US 2001/0014791 A1 Aug. 16, 2001

Related U.S. Application Data

(60) Provisional application No. 60/180,645, filed on Feb. 7, 2000.

(30) Foreign Application Priority Data

Jan. 28, 2000 (DK) .................................. 2000 00138

(51) Int. Cl.[7] ............................................. A61M 5/00
(52) U.S. Cl. ...................................... 604/207; 604/211
(58) Field of Search ................... 604/207, 208, 604/209, 210, 211

(56) References Cited

U.S. PATENT DOCUMENTS

| | | | | |
|---|---|---|---|---|
| 4,498,904 A | * | 2/1985 | Turner et al. ............... | 604/211 |
| 5,284,480 A | * | 2/1994 | Porter et al. .................. | 604/97 |
| 5,674,204 A | * | 10/1997 | Chanoch ..................... | 604/211 |
| 5,679,111 A | * | 10/1997 | Hjertman et al. ........... | 604/135 |
| 5,685,864 A | * | 11/1997 | Shanley et al. ............. | 604/211 |
| 5,725,508 A | * | 3/1998 | Chanoch et al. ............ | 604/207 |
| 5,921,966 A | * | 7/1999 | Bendek et al. .............. | 604/207 |
| 5,947,934 A | | 9/1999 | Hansen et al. .............. | 604/207 |
| 6,048,336 A | | 4/2000 | Gabriel ....................... | 604/211 |
| 6,074,372 A | * | 6/2000 | Hansen ........................ | 604/211 |
| 6,086,567 A | * | 7/2000 | Kirchhofer et al. ......... | 604/211 |
| 6,096,010 A | * | 8/2000 | Walters et al. .............. | 604/207 |
| 6,193,698 B1 | * | 2/2001 | Kirchhofer et al. ......... | 604/211 |
| 6,379,339 B1 | * | 4/2002 | Klitgaard et al. ........... | 604/207 |

FOREIGN PATENT DOCUMENTS

| | | |
|---|---|---|
| DE | 42 08 677 A1 | 9/1993 |
| DK | 168364 B1 | 3/1994 |
| WO | WO 98/10813 | 3/1998 |
| WO | WO 99/64092 | 12/1999 |

\* cited by examiner

*Primary Examiner*—Henry O. Yuen
*Assistant Examiner*—Frederick C Nicolas
(74) *Attorney, Agent, or Firm*—Marc A. Began, Esq.; Richard W. Book, Esq.; Reza Green, Esq.

(57) ABSTRACT

Described is a dose setting limiter for medical injectors of the type having a housing accommodating an ampoule-containing medicine sufficient for a number of dosed injections, a rotary dose setting knob, which is rotational relative to the housing and by which doses may be set by rotating the dose setting knob and an injection button which, when activated, administers the set dose. The dose setting limiter includes a stationary first part connected to the housing, and a second part fitted over the rotary dose setting knob, the second part being able to rotate together with the dose setting knob when setting up a dose and the second part being rotational relative to the first part. A third part is placed between the first part and the second part, the third part having means cooperating with means on the second part for limiting the dose setting.

16 Claims, 2 Drawing Sheets

DOSE SETTING LIMITER

CROSS-REFERENCE TO RELATED APPLICATIONS

This application claims priority under 35 U.S.C. 119 of Danish application no. PA 2000 00138 filed on Jan. 28, 2000, and U.S. provisional application no. 60/180,645 filed on Feb. 7, 2000, the contents of which are fully incorporated herein by reference.

1. Field of the Invention

The present invention relates to a dose setting limiter for medical injectors of the type having a housing accommodating an ampoule containing medicine sufficient for a number of dosed injections, a rotary dose setting knob, which is rotational relative to the housing and by which doses may be set by rotating the dose setting knob and an injection button which, when pressed, administers the set dose.

2. Description of the Related Art

Commercially accessible medical injectors of the above-mentioned type are normally capable of being set to dispense a wide range of doses. Some medication, such as insulin, is often self-administered. The typical diabetes patients will require injections of insulin several times during the course of the day. Normally the size of the doses is prescribed and the dose setting knob of the injection device is therefore always rotated to the same amount before each injection. Due to this there is a great need for an auxiliary dose setting limiter, which can be applied to a medical injector, and which can help setting up the exact same dose every time.

An auxiliary dose setting limiter of this kind is known from WO 99/64092. This dose setting limiter is cup-shaped and is placed retentively over the dose setting knob in a position where a projection on the dose setting limiter aligns the desired dose. When in use, the injection dose is first being set by rotating the dose setting knob, which knob can only be rotated until the pre-set dose is reached, while the projection on the dose setting limiter will be arrested by a stationary raised stud on the injection pen. This known dose setting limiter can only be applied to a traditional pencil-shaped injection device of the type having the dose setting knob placed at the rear end of the pen and a stationary raised stud indicating the zero mark of the scale.

SUMMARY OF THE INVENTION

It is an object of the invention to provide a dose setting limiter, which can be fitted on to a large variety of injection devices. It is a particular object to provide a dose setting limiter that can be fitted on to the new generation of very short injection devices e.g. known from U.S. Pat. No. 5,947,934.

This is obtained by a dose setting limiter for medical injectors of the type having a housing accommodating an ampoule containing medicine sufficient for a number of dosed injections, a rotary dose setting knob, which is rotational relative to said housing and by which doses may be set by rotating said dose setting knob and an injection button which, when activated, administers the set dose, said dose setting limiter comprising:

a stationary first part connected to said housing, and a second part fitted over said rotary dose setting knob, said second part being able to rotate together with said dose setting knob when setting up a dose and said second part being rotational relatively to said first part, which dose setting limiter according to the invention has a third part placed between said first part and said second part, said third part having means cooperating with means on said second part for limiting the dose setting.

The desired dose is first set by rotating the third part with the auxiliary dose setting limiter disconnected from the injection device. When the marker on the third part is positioned in alignment with the desired dose indicated on the scale and the dose setting limiter is fitted on to the injection device, the position of the protrusion on the third part is locked relatively to the shell, due to the friction between the two parts. When setting up a dose by rotating the dose setting dial, the protrusion on the dose setting dial will be arrested by the protrusion on the third part when the predetermined dose is being reached.

The third part need not be loose and rotational, but could be permanently fastened to the shell. The permanent location of the protrusion on the third part would then be the maximal dose, which could be dialed up when the particular shell is connected to the injection device. Different dose setting limiters each having a different maximal dose setting could be made available for the consumer. This would present a very attractive solution for parents wanting to set a maximal dose on the injection device for a child.

In one embodiment of the dose setting limiter according to the invention the third part can move freely when the first part is disconnected from the housing of the injection device, but is locked to the first part when the first part is connected to said housing. The locking is usually done by friction between the injection device, but the ring and the shell could also be preformed by a tooth gearing between the shell and the ring, the ring e.g. having pawls being arrested in depressions in the shell, or by other adequate means arresting the ring when the shell is being connected to the injection device.

The locking is, according to another embodiment of the dose setting limiter, done by a number of holes in the third part being arrested by a number of raised studs on the inside surface of the first part. With the shell being disconnected from the injection device, the user is provided with a clicking feeling, and a click sound, when the ring is rotated relative to the shell, due to the engagement between the holes in the ring and the raised studs on the shell.

In a preferred embodiment of the dose setting limiter according to the invention the means located on the second part and the means on the third part are protrusions. Protrusions are easily manufactured and abut one another in a useful manner.

The third part is, according to yet another embodiment of the dose setting limiter, a flat circular ring fitted inside the first part and the protrusion protrudes inwardly pointing towards the center of the circular ring. By making the third part as a flat ring the thickness of the dose setting limiter can be kept very little. Due to this the total size of the injection device is almost unchanged when the auxiliary dose setting limiter is connected to the injection device.

In a fifth embodiment of the dose setting limiter according to the invention the second part, forming a dose setting dial, is circular and rotational connected to the first part and has the protrusion protruding outwardly. By making the dose setting dial circular it fits onto a large variety of injection devices, while such devices traditionally have a circular dose setting knob.

In yet another embodiment of the dose setting limiter according to the invention the first part, forming a shell, is circular and has a plurality of flanges that fit retentively around said housing, thereby locking said shell to said housing. The shell can be made to fit very tightly to the injection device, making it almost impossible for people with only limited physical strength to remove the dose setting limiter. In that way parental setting of a predetermined dose is irreversible for a child.

In a further embodiment of the dose setting limiter according to the invention the shell has an area on the circular periphery cut off, making the ring accessible for rotation relative to the shell. This allows the user to get a good grip with the fingers on the ring when setting up a dose.

In yet a different embodiment of the dose setting limiter according to the invention the shell is transparent and the ring has a marker visible through the shell, which marker indicates the location of the protrusion on the ring. Since the marker is visible through the transparent shell the preset dose can easily be read on the scale of the shell.

According to the last embodiment of the dose setting limiter according to the invention the dose setting dial can only be rotated until the protrusion on the dose setting dial is arrested by the protrusion on said ring. With the ring being locked onto the shell it is impossible to rotate the dose setting dial beyond the predetermined dose.

BRIEF DESCRIPTION OF THE DRAWINGS

The invention will be explained more fully below in connection with a preferred embodiment and with reference to the drawings in which.

The figures are schematic and simplified for clarity, and they just show details that are essential to the understanding of the invention, while other details are omitted. Throughout, the same reference numerals are used for identical or corresponding parts.

DETAILED DESCRIPTION OF THE EMBODIMENTS

Figure 1:
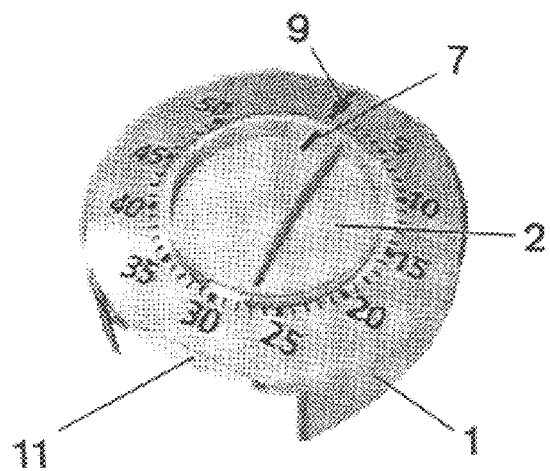
FIG. 1. Shows the auxiliary dose setting limiter according to the invention disconnected from the injection device.
Figure 2:
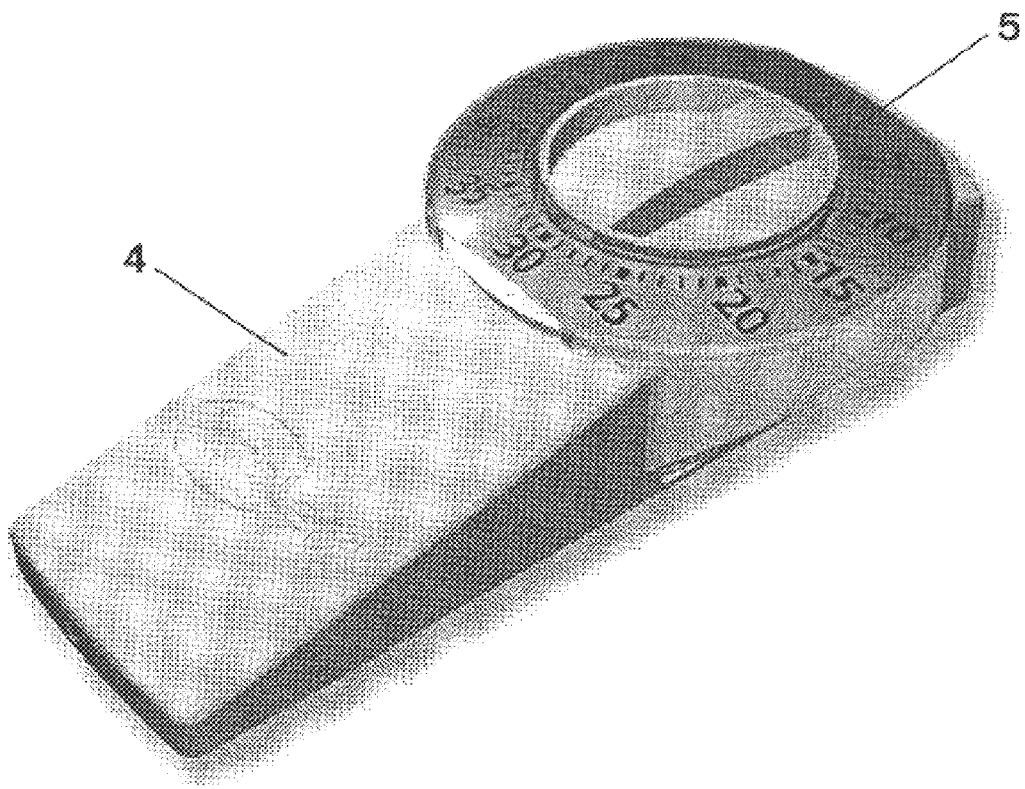
FIG. 2. Shows the auxiliary dose setting limiter according to the invention filted onto a short injection device.
Figure 3:
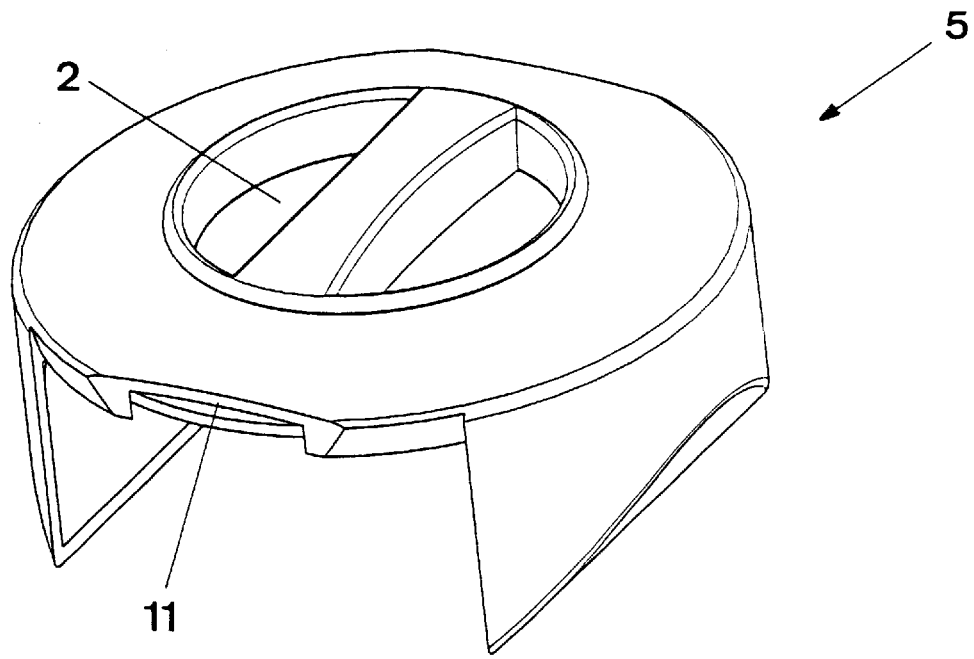
FIG. 3. Shows the auxiliary dose setting limiter according to the invention.
Figure 4:
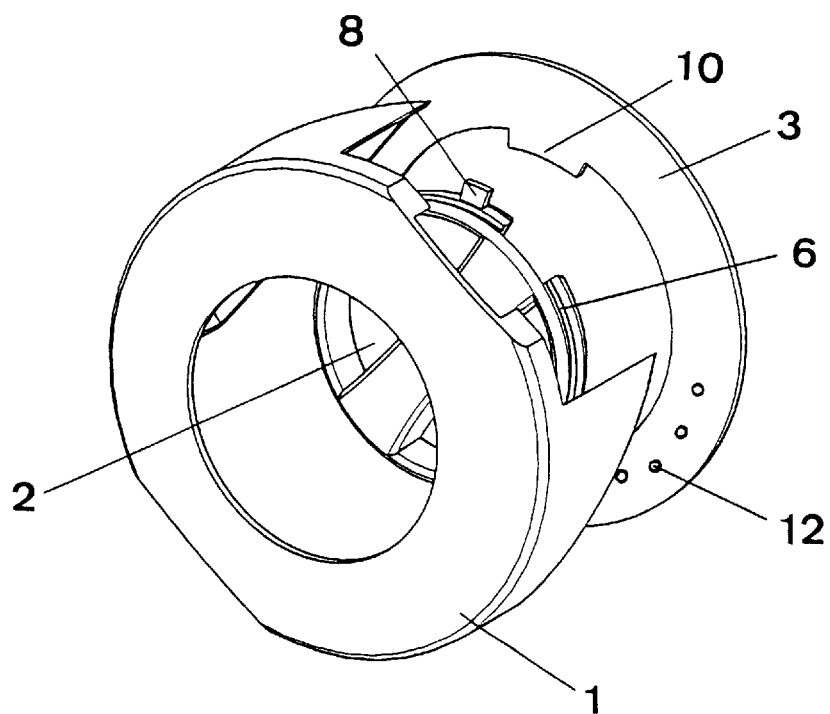
FIG. 4. Shows an exploded view of the auxiliary dose setting limiter according to the invention.

The auxiliary dose setting limiter 5 shown in FIGS. 1 to 4 comprises three parts 1, 2, 3. A stationary first part 1 forms a shell, which is fitted over the injection device 4. The shell 1 is made up from a transparent scale-part carrying a scale indicating the doses and having flanges that fit retentively over the sides of the injection device 4, thereby locking the shell 1 on to the injection device 4. The flanges can be provided with a gripping part that abuts the backside of the injection device.

The second part 2 is the dose setting dial, which fits over the dose setting knob of the injection device and is rotated together with this dose setting knob when setting up a dose. The dose setting dial 2 has a recession 6 into which the shell 1 is placed thereby connecting the shell 1 and the dose setting dial 2 together while allowing the dose setting dial 2 to rotate relative to the shell. The dose setting dial 2 is marked with a pointer 7, which in cooperation with the stationary scale on the shell 1 indicates the set dose. Located on the periphery of the dose setting dial is a protrusion 8 protruding outwardly. This protrusion 8 is placed adjacent the pointer 7 on the dose setting dial 2.

The third part 3 is a flat circular ring, which is placed in a not shown recession on the backside of the shell 1. Depending on the width of the ring 3 it can be captured between the shell 1 and the dose setting dial 2. The ring 3 can rotate freely relative to both the shell and the dose setting dial 2 when the shell 1 is disconnected from the injection device 4. When the user connects the dose setting limiter 5 to the injection device 4, the ring 3 is locked to the shell 1 making the ring 3 non-rotational relative to the shell 1. The locking is done by friction between the injection device 4, the ring 3 and the shell 1. To increase the friction the ring 3 is equipped with a number of holes 12 that are arrested by one or more not shown raised studs placed on the inside surface of the shell 1. One such hole 12 could be provided for each dial indicated on the transparent scale-part. A not shown tooth gearing between the shell 1 and the ring 3 can also perform the locking. The ring 3 is equipped with a protrusion 10 protruding inwardly and pointing towards the center of the ring 3. This protrusion 10 has the same width as the finger grip on the dose setting dial 2 and carries a marker 9 indicating the center of the protrusion 10.

In use the auxiliary dose setting limiter 5 is set while being disconnected from the injection device. The setting of the desired dose is simply done by rotating the ring 3 relative to the shell 1 until the marker 9 is placed over the correct dose indication on the scale located on the shell 1. For accommodating an easy rotation of the ring 3, the shell 1 has two areas 11 on the circular periphery cut off for allowing the fingers of the user to grip on the ring 3.

When the correct dose has been pre-set the dose setting limiter 5 is placed onto the injection device 4 by pressing the two flanges over the housing of the injection device 4. This operation locks the ring 3 on to the shell 1. The injection device 4 with the auxiliary dose setting limiter 5 is now ready for use. The next time the user sets up a dose by rotating the dose setting dial 2, the protrusion 8 on the dose setting dial 2 will be arrested by the protrusion 10 on the ring 3 when the pre-set dose has been reached. In this way it may be ensured that a set maximum dose is not exceeded. With the described placements of the two protrusions 8, 10 the set dose will be the dose indicated on the scale, but other placements of the protrusion 8, 10 are possible. If desired, other means instead of protrusions 8, 10 could be used. The means could be a raised stud placed on the dose setting dial 2 and a depression placed on the ring 3 or vice versa, while the two parts 2, 3 could overlap each other. The ring 3 could be permanently fastened to the shell 1, e.g. by providing the not shown raised studs located on the inside surface of the shell 1 with barbs or other retention means at their outer ends, thereby preventing removal of the ring once it has been connected to the shell 1. The two parts 1, 3 could even be moulded as a unitary part. The protrusion 10 would then have a permanent location on the shell indicating the maximal dose, which can be dialed up on the injection device carrying the particular dose setting limiter 5. It would then be necessary to provide the user with different dose setting limiters 5 each having a different maximal dose setting. Parents could then provide the injection device used by their child with a dose setting limiter 5 having a predetermined maximal dose suitable for that individual child. In this way children performing self-injections would not be able to administer a dose large than predetermined by the parents.

Some preferred embodiments have been shown in the foregoing, but it should be stressed that the invention is not limited to these, but may be embodied in other ways within the subject matter defined in the following claims.

Although the present invention has been described in connection with a very short injection device 4 it is obvious that the dose setting limiter 5 as defined in the claims, with some minor adjustments can be used for a large variety of injection devices 4.

What is claimed is:

1. A dose setting limiter for a medical injector, the dose setting limiter comprising:

three circular parts: a shell-shaped first part; a second part; and a third part; the three parts being coaxially assembled and sharing a common center axis; wherein:
the shell-shaped first part has a circular upper surface and is connectable to the injector;
the second circular part is rotatable for setting up a dose and has a periphery from which a protrusion extends radially;
the third part:
is shaped as a flat ring sandwiched between the first and second part;
is rotatable about the common centre axis with respect to the first part when the dose setting limiter is disconnected from the injector but rotationally locked to the first part when the first part is connected to the injector,
further comprises another protrusion that cooperates with the protrusion located on the second part for limiting the angular rotation of the second part relative to the third part when the second part is rotated to set up a dose.

2. The dose setting limiter according to claim 1, wherein: the second part forms a dose setting dial, is coaxially secured to the first part, and is accessible to a user through an opening in the first part.

3. The dose setting limiter according to claim 1, wherein the third part is locked to the first part by a plurality of holes in the third part being arrested by a number of raised studs on an inside surface of the first part when the third part is axially pressed toward the first part.

4. The dose setting limiter according to claim 1, wherein the protrusion on the second part protrudes outward from the common centre and the another protrusion on third part protrudes inward toward the common centre.

5. The dose setting limiter according to claim l, wherein first part has a periphery an upper surface on the periphery has an area that that has a cut off, thereby making the third part accessible to a user to rotate the third part relative to the first part.

6. The dose setting limiter according to claim 5, wherein the first part is at least partially transparent and the third part has a marker visible through the first part, marker indicating the location of the another protrusion on the third part.

7. A dose setting limiter for use in an injector, the dose setting limiter comprising:
a first part that may be connected to the injector;
a second part that is rotatable for setting up a dose, the second part being rotatable relative to the first part and comprising a dose limiting means for limiting a dose setting;
a third part located between the first and second part, the third part comprising a cooperating means for cooperating with the dose limiting means of the second part, to limit the dose setting;
wherein the third part is capable of moving freely when the first part is disconnected from the injector but is locked to the first part when the first part is connected to the injector.

8. The dose setting limiter according to claim 7, wherein the dose limiting means of the second part comprises a protrusion.

9. The dose setting limiter according to claim 8, wherein the cooperating means also comprises a protrusion.

10. The dose setting limiter according to claim 7, wherein the third part is locked to the first part by a number of holes in the third part that are arrested by a number of raised studs on the inside surface of the first part.

11. The dose setting limiter according to claim 7, wherein the first part forms a circular shell.

12. A dose setting limiter for use in an injector, the dose setting limiter comprising:
a first part that may be connected to the injector;
a second part that is rotatable for setting up a dose, the second part being rotatable relative to the first part and comprising a dose limiting means for limiting a dose setting;
a third part located between the first and second part, the third part comprising a cooperating means for cooperating with the dose limiting means of the second part to limit the dose setting; wherein the first part forms a shell, is circular, and has a plurality of flanges that fit retentively around a portion of the injector thereby locking the shell to the injector.

13. The dose setting limiter of claim 12, wherein the shell has a periphery with an area cut off, thereby making the third portion accessible for rotation relative to the shell.

14. The dose setting limiter of claim 13, wherein the shell is transparent and the third part has a marker visible through the shell, the marker indication the locations of the cooperating means on the third part.

15. The dose setting limiter of claim 13, wherein at least one of the cooperating means and the dose limiting means comprises a protrusion.

16. The dose setting limiter of claim 13, wherein the cooperating means and dose limiting means comprise protrusions and wherein the protrusion on the second part protrudes outward from the common centre and the protrusion on the third part protrudes inward toward the common centre.

* * * * *